017# United States Patent [19]

Schrider et al.

[11] 4,052,381

[45] Oct. 4, 1977

[54] SUBSTITUTED PHOSPHOROTHIOIC ACID AND METHOD OF USE IN SIPHONAPTERA COMPOSITIONS IN WARM-BLOODED ANIMALS

[75] Inventors: Michael Stanley Schrider, South Bound Brook; Stephen David Levy, Trenton, both of N.J.

[73] Assignee: American Cyanamid Company, Stamford, Conn.

[21] Appl. No.: 570,295

[22] Filed: Apr. 21, 1975

[51] Int. Cl.$^2$ ............................................ C07C 107/06
[52] U.S. Cl. ..................................... 260/206; 424/226
[58] Field of Search ................. 260/206, 205; 424/226

[56] References Cited

U.S. PATENT DOCUMENTS 2,947,663  8/1960  Losco et al. ..................... 260/206 X

*Primary Examiner*—Charles F. Warren
*Attorney, Agent, or Firm*—Norton S. Johnson

[57] ABSTRACT

This invention relates to phosphorothioic acid, O,O'-azodi-p-phenylene O,O,O',O' tetramethyl ester, trans and its use in siphonaptera compositions in warm-blooded animals.

1 Claim, No Drawings

SUBSTITUTED PHOSPHOROTHIOIC ACID AND METHOD OF USE IN SIPHONAPTERA COMPOSITIONS IN WARM-BLOODED ANIMALS

SUMMARY OF THE INVENTION

This invention relates to phosphorothioic acid, O,O'-azodi-p-phenylene O,O,O',O' tetramethyl ester, trans and its use in siphonaptera compositions, in particular as a pesticide to control fleas on warm-blooded animals.

The active component of the present invention can be illustrated by the following structure:

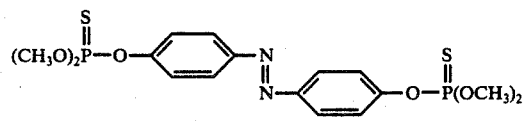

The compound phosphorothioic acid, O,O'-azodi-p-phenylene ester, trans may be prepared by reacting the diphenol:

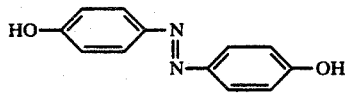

with at least 2 moles of O,O-dimethyl phosphorohalidothioate represented by the formula:

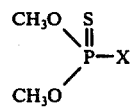

wherein X is halogen, preferably chlorine.

The reaction between the diphenol and the O,O-dimethyl phosphorohalidothioate is carried out on a relative mole basis of one mole of the diphenol to at least 2 moles of the phosphorohalidothioate, although up to 4 moles of the phosphorohalidothioate may be employed to advantage, under alkaline conditions and in the presence of a polar solvent such as water, methyl ethyl ketone, and the like, at a temperature of from between 0° C. and 100° C. This compound may also be prepared in solvents having a wide range of polarity employing a variety of methods to prevent the accumulation of hydrogen halide by-product.

We have now found that the compound phosphorothioic acid, O,O'-azodi-p-phenylene O,O,O',O'-tetramethyl ester, trans in highly effective topically and systemically in controlling fleas.

The use of phosphorothioic acid, O,O'-azodi-p-phenylene ester, trans to control the infestation or reinfestation of dogs and cats by fleas is a novel use of this material. The use of the aforementioned compound to control insect pests, particularly fleas on dogs and cats is novel.

It is known that O,O-diethyl O-(2-isopropyl-6-methyl-4-pyrimidinyl)phosphototothiate (Diazinon) and O,O-dimethyl S-(1,2-dicarbethoxyethyl)dithiophosphate (Malathion) are among the insecticides currently used as sprays to control lice on cattle, but it is usually recommended that two applications of these materials be made within a few weeks of each other. The use of O,O-diethyl O-(3,5,6-trichloro-2-pyridyl)phosphorothioate (Dursban chloropyrifos) has been reported by Buchanan et al., New Zealand Vet. Journal 19 (9): 197–202 (1971), to give effective control of lice on cattle with a single spray treatment.

The control of infestations of fleas or reinfestations of the same, is most desirable because of the economic losses caused by these pests.

Typically, such insects include fleas (Siphonaptera) such as Ctenocephalides canis and Ctenocephalides felis on dogs and cats.

The use of phosphorothioic acid O,O'-azodi-p-phenylene O,O,O',O'-tetramethyl ester, trans to control infestations of fleas on warm-blooded animals would be particularly advantageous because it is substantially non-toxic at concentrations many times that of the actual amounts employed. The active ingredient, phosphorothioic acid O,O'-azodi-p-phenylene O,O,O',O'-tetramethyl ester, trans, may be conveniently formulated as dusts, dust concentrates, wettable powders, emulsifiable concentrates, PVC collars and as solutions, with conventional solid or liquid adjuvants. It may also be incorporated in feed or in an animal treat which is highly palatable to the animal. Wettable powders and emulsifiable concentrates are particularly useful since they can be diluted with water and applied topically as dilute liquid sprays to the animals which are to be protected from attack. In the latter situation, the dilute liquid formulations may also be used as dips as well as sprays.

Dusts or dust concentrates can be prepared by grinding together the inert solid diluent such as attapulgite, kaolin, walnut shell flour, diatomaceous earth, ground corn cob grits, or ground coconut shell, and the active ingredient, where such active ingredient is in solid form. Where the active ingredient is liquid, it may be sprayed on the carrier and thoroughly mixed with it or it may be dissolved in a solvent such as acetone, xylene, lard or vegetable oils and the solution sprayed on the solid carrier. Dusts usually contain from about 1% to 15% by weight of acitve ingredient, whereas concentrates may contain from about 16% to about 85% by weight of the active material.

Solutions in organic solvents such as various ketones, lower monohydric aliphatic alcohols, ketoalcohols such as diacetone alcohol, various esters, aromatic and aliphatic hydrocarbons may be applied as a spray or pour-on.

Wettable powders are prepared in the same fashion as dust concentrates, except that about 5% to 10% by weight of a surfactant, and 5% to 10% of a dispersing agent are included therein.

The active compound of the present invention may also be prepared as emulsifiable concentrates by dissolving or dispersing about 10% to 75% by weight of the active compound in a suitable solvent or carrier such as a petroleum distillate having a minimum aromatic content of 85% and admixing therewith about 10% by weight of an emulsifier such as polyoxyethylene derivatives and blends with alkyl aryl sulfonates. These concentrates are also generally dispersed in water or other suitable solvent for application.

Application of the active compound can be made either directly, as by dusting, dipping and spraying, or by pour-on, or from pressure spray cans.

Application to warm-blooded animals, such as dogs and cats, to control fleas can be effected by spraying each animal with 20 cc. of aqueous solutions containing from 0.0375% to 0.355% (w/v) [0.355% (w/v) contains 0.355 gram of active ingredient per 100 grams of solution] to provide from 1.25 milligrams to 10 milligrams of active material per kilogram of body weight.

Application to dogs and cats to control fleas can also be effected by treating each animal with a dust containing about 2% active compound to provide from 10 milligrams to 120 milligrams of active compound per kilogram of body weight.

The active compound of the present invention can be administered to dogs and cats in from 0.5 to 400 mg./kg. of body weight in a physiologically acceptable diluent, including, for example, cat and dog food, gelatin and the like.

For systemic control of fleas on warm-blooded animals, such as cats and dogs, the active compound can be incorporated in the animal feed in sufficient amount to provide about 25 ppm to 1000 ppm and preferably 75 ppm to 300 ppm of said compound in the feed. This can be accomplished by dispersing the active compound in a vegetable oil or fat and spraying this prepared mixture on an edible feed meal such as soybean meal.

In practice, the feed containing the anti-flea compound should provide the warm-blooded animal with from 3 to 50 mg./kg./day of said compound for long term feeding, for example, for from several weeks to several months or continuously. Diets providing from 50 to 400 mg./kg./day will generally be administered for periods of short duration, i.e., 1 to 10 days. Weights given as mg./kg./day means mg./kg. of animal body weight per day.

It is, of course, obvious that the active compound may also be administered orally in the form of a pill, tablet, capsule or oral liquid using traditional carriers and excipients. Dosages should provide the mg./kg./day requirements given above with respect to administration in the feed.

SPECIFIC DISCLOSURE

The present invention is illustrated by the following examples. All parts and percentages are by weight unless otherwise specifically designated.

EXAMPLE 1.

Preparation of phosphorothioic acid, O,O'-Azodi-p-phenylene O,O,O',O' tetramethyl ester, trans An amount of 10.3 grams (0.048 mole) of 4(4'-hydroxybenzene-azo) phenol trans [Willstatter et al, Ber. 39, 349 (1939)] is dissolved in 150 ml. of tertiary butanol at 70° C., and a solution of 10.8 grams (0.096 mole) of potassium tertiary butoxide in 100 ml of tertiary butanol is added theret followed by the addition of 17.0 grams (0.105 mole) of O,O-dimethyl phosphorochloridothioate. The reaction mixture is refluxed for 1 hour, then stripped and the residue is dissolved in benzene. The benzene solution is then extracted successively with water, dilute sodium hydroxide and water. The benzene extract is dried and concentrated to obtain 24 grams of an orange-colored solid. This material is recrystallized from 350 ml of hot isopropanol to obtain 13.6 grams of a golden orange-colored solid, melting point 121°–122° C. Anal. calc for $C_{16}H_{20}N_2P_2S_2$ (in percent): C, 42.85; H, 4.50; P, 13.82; S, 14.30. Found: C, 42.84; H, 4.77; P, 13.69; S, 14.05.

EXAMPLE 2

Siphonaptericidal Activity

The efficacy of the present compound of this invention in controlling fleas is demonstrated in the following example utilizing the species Ctenocephalides felis. In these tests, ten adult fleas are sprayed for 30 seconds with an acetone/water solution containing 1.0 ppm of the test compound. After this treatment, the fleas are maintained for 48 hours at room temperature and 80% relative humidity. At the end of this period the efficacy is reported as percentage of the group killed. The compound phosphorothioic acid, O,O'-azodi-p-phenylene O,O,O',O' tetramethyl ester, trans in the above test gave 70% mortality.

WHAT IS CLAIMED:

1. The compound phosphorothioic acid, O,O'-azodi-p-phenylene O,O,O',O' tetramethyl ester, trans.

* * * * *